US007833536B2

(12) United States Patent
Frey et al.

(10) Patent No.: US 7,833,536 B2
(45) Date of Patent: Nov. 16, 2010

(54) MYCOPLASMA SUBUNIT VACCINE

(75) Inventors: Joachim Frey, Bern (CH); Edy M. Vilei, Urtenen-Schönbühl (CH); Paola Pilo, Geneva (CH)

(73) Assignee: University of Bern, Bern (CH)

( * ) Notice: Subject to any disclaimer, the term of this patent is extended or adjusted under 35 U.S.C. 154(b) by 0 days.

(21) Appl. No.: 11/994,677

(22) PCT Filed: Jul. 6, 2006

(86) PCT No.: PCT/EP2006/063948

§ 371 (c)(1),
(2), (4) Date: Jan. 4, 2008

(87) PCT Pub. No.: WO2007/006712

PCT Pub. Date: Jan. 18, 2007

(65) Prior Publication Data

US 2008/0193463 A1    Aug. 14, 2008

Related U.S. Application Data

(63) Continuation of application No. 11/176,700, filed on Jul. 7, 2005, now abandoned.

(51) Int. Cl.
*A61K 39/02* (2006.01)
*A61K 39/00* (2006.01)
*A61K 39/116* (2006.01)
*C12P 1/00* (2006.01)
*C07K 14/00* (2006.01)

(52) U.S. Cl. .............. 424/264.1; 424/184.1; 424/185.1; 424/203.1; 435/41; 530/350

(58) Field of Classification Search .................. None
See application file for complete search history.

(56) References Cited

FOREIGN PATENT DOCUMENTS

| WO | 2002089838 A1 | 11/2002 |
| WO | WO 02/089838 A1 * | 11/2002 |
| WO | 2004101795 A1 | 11/2004 |

OTHER PUBLICATIONS

Vilei et al, Mycoplasmal infections:Molecular analysis of virulence attributes of bovine Mycoplasma species, Institute of Veterinary Bacteriology, University of Bern, Annual Report 2003, pp. 1-7 and 12-14 only.*
Greenspan et al. (Nature Biotechnology 7: 936-937, 1999).*
Bowie et al (Science, 1990, 257:1306-1310).*
Ellis (Vaccines, W.B. Saunders Company, 1988, Chapter 29).*
Boslego et al (Vaccines and Immunotherapy, Pergaman Press, 1991, Chapter 17).*
Fernald et al (Infection and Immunity, Jun. 1970, vol. 1, No. 6, p. 559-565).*
Brennan, P.C. et al. (Jun. 1969). Relationship of Hydrogen Peroxide Production by Mycoplasma pulmonis to Virulence for Catalase Deficient Mice. Journal of Bacteriology. 98(3):1036-1040.
Pilo, P. et al. (Oct. 2005). A Metabolic Enzyme as a Primary Virulence Factor of Mycoplasma mycoides subsp. mycoides Small Colony. Journal of Bacteriology. 187(19):6824-6831.
Thiaucourt, F. et al. (2003). Contagious Bovine Pleuropneumonia Vaccines, Historic Highlights, Present Situation and Hopes. Developments in Biologicals. 114:147-160.
Djordjevic, S.P. et al. (2003). Characterization of a chromosomal region of Mycoplasma sp. bovine group 7 strain PG50 encoding a glycerol transport locus (gtsABC). Microbiology. 149:195-204.
Houshaymi, B.M. et al. (Feb. 1997). Oxidation of glycerol differentiates African from European isolates of Mycoplasma mycoides subspecies mycoides SC (small colony). The Veterinary Record. 140(7):182-183.
Vilei, E.M. et al. (Jan. 2001). Genetic and Biochemical Characterization of Glycerol Uptake in Mycoplasma mycoides subsp. mycoides SC: Its Impact on H2O2 Production and Virulence. Clinical and Diagnostic Laboratory Immunology. 8(1):85-92.
Westberg, J. et al. (2004). The Genome Sequence of Mycoplasma mycoides subsp. mycoides SC Type Strain PG1T, the Causative Agent of Contagious Bovine Pleuropneumonia (CBPP). Genome Research. 14(2):221-227.

* cited by examiner

*Primary Examiner*—Vanessa L. Ford
(74) *Attorney, Agent, or Firm*—William M. Blackstone

(57) ABSTRACT

The present invention relates i.a. to vaccines for combating *Mycoplasma* infection, to mycoplasmal L-α-glycerophosphate oxidase for use in such vaccines, to the use of mycoplasmal L-α-glycerophosphate oxidase for the manufacturing of such vaccines, to methods for the preparation of such vaccines and to diagnostic tests for the discrimination of animals vaccinated with said vaccines and animals vaccinated with whole cell vaccines or animals suffering from field infection.

11 Claims, 4 Drawing Sheets

MYCOPLASMA SUBUNIT VACCINE

Figure 1:
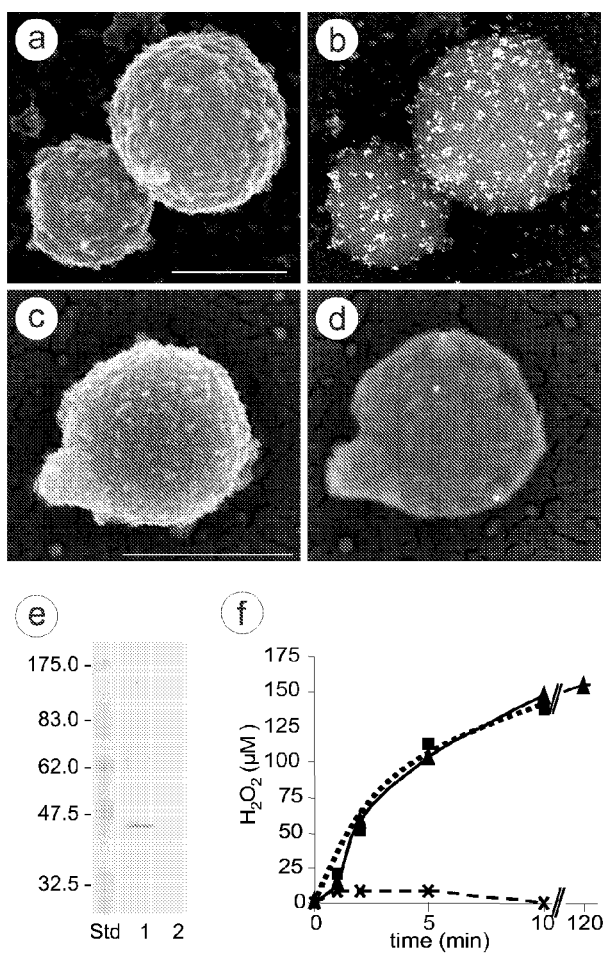

The present invention relates i.a. to vaccines for combating *Mycoplasma* infection, to mycoplasmal L-α-glycerophosphate oxidase for use in such vaccines, to the use of mycoplasmal L-α-glycerophosphate oxidase for the manufacturing of such vaccines, to methods for the preparation of such vaccines and to diagnostic tests for the discrimination of animals vaccinated with said vaccines and animals vaccinated with whole cell vaccines or animals suffering from field infection.

During evolution, pathogenic bacteria have developed complex interactions with their hosts. This has frequently involved the acquisition of virulence factors on pathogenicity islands, plasmids, transposons or prophages, allowing them to colonize, survive and replicate within the host. In contrast, *Mycoplasma* species, the smallest self-replicating organisms, have regressively evolved from Gram-positive bacteria by reduction of the genome to a minimal size, with the consequence to economize their genetic resources.

*Mycoplasma* species represent the smallest self-replicating organisms detected on earth. Their genomes range from 580 kilo base pairs (kb) in *Mycoplasma genitalium* (Fraser, C. M. et al., 1995, Science 270: 397-403) to 1358 kb in *Mycoplasma penetrans* (Sasaki, Y. et al, 2002, Nucleic Acids Res. 30: 5293-5300) This leads to drastic economization of genetic resources and to an obligate parasitic lifestyle. Pathogenic *Mycoplasma* species cause mainly atypical pneumonia, urogenital infections and arthritis in humans and in animals (Baseman, J. B., and J. G. Tully, 1997, Emerg. Infect. Dis. 3: 21-32, Blanchard, A., and G. F. Browning (eds.). 2005. *Mycoplasmas*: Molecular biology, pathogenicity and strategies for control. Horizon Bioscience, Wymondham, U.K., Frey, J. 2002. Mycoplasmas of animals, p. 73-90. In S. Razin and R. Herrmann (eds.), Molecular biology and pathogenicity of mycoplasmas. Kluwer Academic/Plenum Publishers, New York). It is stressed here, that due to the fact that there are *Mycoplasma* species known that infect humans (e.g. *M. genitalium, M. pneumoniae*), bovine species (e.g. *M. sp* bovine group 7), pigs (e.g. *M. hyopneumoniae*) or poultry (e.g. *M. gallisepticum*), where in the text it says animals, this should be interpreted as to include i.a. humans, bovine species, pigs and poultry.

In contrast to other pathogenic bacteria where virulence is mostly determined by toxins, invasins, and cytolysins, pathogenic *Mycoplasma* species appear to have no such typical primary virulence factors, as revealed by the genomic sequence analysis of the eight species completely sequenced (Chambaud, I. et al, 2001, Nucleic Acids Res. 29: 2145-2153, Fraser ET AL., 1995, Science 270: 397-403, Himmelreich, R. et al., 1996, Nucleic Acids Res. 24: 4420-4449, Jaffe, J. D. et al, 2004, Genome Res. 14: 1447-1461, Minion, F. C. et al., 2004, J. Bacteriol. 186: 7123-7133, Papazisi, L. et al, 2003, Microbiology 149: 2307-2316, Sasaki, Y. et al., 2002, Nucleic Acids Res. 30: 5293-5300, Westberg, J. et al., 2004, Genome Res. 14: 221-227)

Although diagnosis of mycoplasmal infections has improved significantly since the introduction of PCR methods and antigenic variability has been studied in detail in several *Mycoplasma* species, there is currently very little knowledge available on the molecular mechanisms and the effectors that allow pathogenic mycoplasmas to cause host cell damage, inflammation and disease. Therefore, the development of vaccines that specifically aim at prevention of these unwanted effects is highly needed.

It is an objective of the present invention to provide a vaccine for combating *Mycoplasma* infection, that avoids or diminishes host cell damage, inflammation and disease.

Surprisingly, a novel primary virulence factor was found to be a significant cause of cell injury in *Mycoplasma*. This virulence factor appeared to consist of toxic by-products such as $H_2O_2$ and other accompanying reactive oxygen species (ROS).

It could be shown that the formation of $H_2O_2$/ROS could directly be related to the activity of the enzyme mycoplasmal L-α-glycerophosphate oxidase (GlpO), an enzyme that is involved in the metabolism of glycerol.

Even more unexpectedly, it could be demonstrated that the formation of $H_2O_2$/ROS is the main, if not the only cause of tissue damage caused by *Mycoplasma* infection. This means that now for the first time the main virulence factor of *Mycoplasma* has been defined.

The glycerol metabolic pathway in *Mycoplasma* can not easily be influenced or changed, and therefore, formation of $H_2O_2$/ROS can not easily be changed through modification of the glycerol metabolic pathway in *Mycoplasma* as such. Therefore, the route of developing live attenuated *Mycoplasma* seems, contrary to the situation in non-mycoplasmal species, less feasible.

However, it was now surprisingly found that antibodies reactive with mycoplasmal L-α-glycerophosphate oxidase are capable of suppressing the production of $H_2O_2$/ROS to the extent that little or no damage at all is done to the tissue of infected animals. This opens the way to vaccination with i.a. subunit vaccines as will be explained below.

This is even more surprising given the fact that in all non-mycoplasmal bacteria, enzymes having glycerophosphate oxidase activity are found intracellular, because catalase in these cells breaks down $H_2O_2$ immediately after formation. In such cases, antibodies directed against glycerophosphate oxidase will thus have no effect whatsoever because they can not enter the bacteria. It was found now that contrary to all non-mycoplasmal bacteria, and apparently as a result of the lack of catalase, *Mycoplasma* has during evolution transferred its mycoplasmal L-α-glycerophosphate oxidase from the intracellular space to the membrane, in such a way that it leads to the production of extracellular $H_2O_2$. This therefore is of no harm to the bacterium, but now becomes detrimental to tissues of the infected host. This might explain that in the case of *Mycoplasma*, antibodies against mycoplasmal L-α-glycerophosphate oxidase (contrary to other bacteria) unexpectedly do interfere with the enzyme's activity to release extracellular $H_2O_2$.

The mycoplasmal enzyme mycoplasmal L-α-glycerophosphate oxidase is present in all *Mycoplasma* species known. All further references made to L-α-glycerophosphate oxidase refer to mycoplasmal L-α-glycerophosphate oxidase. In Table 1, below, the EMBL/GenBank accession numbers are presented of the gene encoding the mycoplasmal L-α-glycerophosphate oxidase in strains of the *Mycoplasma* species, *M.* sp. bovine group 7, *M. mycoides* subsp. *Capri, M. penetrans, M. gallisepticum, M. mobile, M. pulmonis, M. hyopneumoniae, M. pneumoniae, M. genitalium.*

Additionally, in the Examples, EMBL/GenBank accession numbers are presented of the genes encoding the mycoplasmal L-α-glycerophosphate oxidase in strains of the *Mycoplasma* species *M. mycoides* S(mall) C(olony) strains Afadé and L2.

Due to the fact that the enzyme mycoplasmal L-α-glycerophosphate oxidase is present in all *Mycoplasma* species known, its use for raising antibodies against this protein for combating *Mycoplasma* infection, more specifically for avoiding or diminishing host cell damage, inflammation and disease, turned out to be generally applicable regardless the *Mycoplasma* species.

The principle of raising antibodies against *Mycoplasma* will be explained in the Examples below.

*Mycoplasma mycoides* subsp. *mycoides* SC, the etiological agent of contagious bovine pleuropneumoniae (CBPP), a severe infectious disease causing major losses of livestock, was used as a model to investigate the molecular ba sis of mycoplasmal virulence. *M. mycoides* subsp. *mycoides* SC is an extra-cellular pathogen with a genome size of 1211 kb (Westberg, J. et al., 2004, Genome Res. 14: 221-227) that lives in close association with the host cells. The rationale for the use of this species as a model is the high virulence of this species as well as the fact that it is clearly established as the etiological agent of CBPP. Furthermore, this severe cattle disease is of extraordinary socio-economic importance to livestock production in countries that currently suffer CBPP outbreaks. In addition, countries that are free of this epidemic are continuously threatened by re-emerging infections.

Because it has now been established that antibodies against mycoplasmal L-α-glycerophosphate oxidase can be used for combating *Mycoplasma* infection, more specifically for avoiding or diminishing host cell damage, inflammation and disease, the next step is the use of mycoplasmal L-α-glycerophosphate oxidase for the generation of antibodies, both in vivo and in vitro. An example of the in vivo use of mycoplasmal L-α-glycerophosphate oxidase is the use in a vaccine. Such a vaccine, when administered, induces antibodies against *Mycoplasma*. This will be discussed in more detail below. En example of in vivo or in vitro use of mycoplasmal L-α-glycerophosphate oxidase is the use for raising antibodies for use in in a vaccine. Such vaccines will also be discussed below.

Alternative vaccines are vaccines based upon live recombinant carriers carrying the gene or a part thereof encoding (an immunogenic part of) mycoplasmal L-α-glycerophosphate oxidase and DNA vaccines comprising the gene or a part thereof encoding (an immunogenic part of) mycoplasmal L-α-glycerophosphate oxidase.

Since the sequences encoding the enzyme mycoplasmal L-α-glycerophosphate oxidase in the various *Mycoplasma* species are known, it is now possible to obtain the enzyme mycoplasmal L-α-glycerophosphate oxidase in sufficient quantities. This can e.g. be done by using expression systems to express the genes encoding these proteins.

An essential requirement for the expression of the gene or a part thereof encoding (an immunogenic part of) mycoplasmal L-α-glycerophosphate oxidase is an adequate promoter functionally linked to the gene, so that the gene is under the control of the promoter. This can be acomplished by means of e.g. standard molecular biology techniques. (Sambrook, J. and Russell, D. W., Molecular cloning: a laboratory manual, 2001. ISBN 0-87969-577-3). It is obvious to those skilled in the art that the choice of a promoter extends to any eukaryotic, prokaryotic or viral promoter capable of directing gene transcription in cells used as host cells for protein expression. Functionally linked promoters are promoters that are capable of controlling the transcription of the nucleic acids to which they are linked.

Such a promoter can be a *Mycoplasma* promoter e.g. the promoter involved in in vivo expression of the gene encoding mycoplasmal L-α-glycerophosphate oxidase, provided that that promoter is functional in the cell used for expression. It can also be a heterologous promoter. When the host cells are bacteria, useful expression control sequences which may be used include the Trp promoter and operator (Goeddel, et al., Nucl. Acids Res., 8, 4057, 1980); the lac promoter and operator (Chang, et al., Nature, 275, 615, 1978); the outer membrane protein promoter (Nakamura, K. and Inouge, M., EMBO J., 1, 771-775, 1982); the bacteriophage lambda promoters and operators (Remaut, E. et al., Nucl. Acids Res., 11, 4677-4688, 1983); the α-amylase (*B. subtilis*) promoter and operator, termination sequences and other expression enhancement and control sequences compatible with the selected host cell.

When the host cell is yeast, useful expression control sequences include, e.g., α-mating factor. For insect cells the polyhedrin or p10 promoters of baculoviruses can be used (Smith, G. E. et al., Mol. Cell. Biol. 3, 2156-65, 1983). When the host cell is of mammalian origin illustrative useful expression control sequences include the SV-40 promoter (Berman, P. W. et al., Science, 222, 524-527, 1983) or the metallothionein promoter (Brinster, R. L., Nature, 296, 39-42, 1982) or a heat shock promoter (Voellmy et al., Proc. Natl. Acad. Sci. USA, 82, 4949-53, 1985).

Bacterial, yeast, fungal, insect and mammalian cell expression systems are very frequently used systems. Such systems are well-known in the art and generally available, e.g. commercially through Invitrogen, Novagen or Clontech Laboratories, Inc. 4030 Fabian Way, Palo Alto, Calif. 94303-4607, USA. Next to these expression systems, parasite-based expression systems are very attractive expression systems. Such systems are e.g. described in the French Patent Application with Publication number 2 714 074, and in US NTIS Publication No US 08/043,109 (Hoffman, S. and Rogers, W.: Public. Date 1 Dec. 1993).

When a protein is used for e.g. vaccination purposes or for raising antibodies, it is however not necessary to use the whole protein. It is also possible to use a fragment of that protein that is capable, as such or coupled to a carrier such as e.g. KLH, of inducing an immune response against that protein, a so-called immunogenic fragment. An "immunogenic fragment" is understood to be a fragment of the full-length protein that still has retained its capability to induce an immune response in the host, i.e. comprises a B- or T-cell epitope. At this moment, a variety of techniques is available to easily identify DNA fragments encoding antigenic fragments (determinants). The method described by Geysen et al (Patent Application WO 84/03564, Patent Application WO 86/06487, US Pat. No. 4,833,092, Proc. Natl Acad. Sci. 81: 3998-4002 (1984), J. Imm. Meth. 102, 259-274 (1987), the so-called PEPSCAN method is an easy to perform, quick and well-established method for the detection of epitopes; the immunologically important regions of the protein. The method is used world-wide and as such well-known to man skilled in the art. This (empirical) method is especially suitable for the detection of B-cell epitopes. Also, given the sequence of the gene encoding any protein, computer algorithms are able to designate specific protein fragments as the immunologically important epitopes on the basis of their sequential and/or structural agreement with epitopes that are now known. The determination of these regions is based on a combination of the hydrophilicity criteria according to Hopp and Woods (Proc. Natl. Acad. Sci. 78: 38248-3828 (1981)), and the secondary structure aspects according to Chou and Fasman (Advances in Enzymology 47: 45-148 (1987) and U.S. Pat. No. 4,554,101). T-cell epitopes can likewise be predicted from the sequence by computer with the aid of Berzofsky's amphiphilicity criterion (Science 235, 1059-1062 (1987) and U.S. patent application NTIS U.S. Ser. No. 07/005,885). A condensed overview is found in: Shan Lu on common principles: Tibtech 9: 238-242 (1991), Good et al on Malaria epitopes; Science 235: 1059-1062 (1987), Lu for a review; Vaccine 10: 3-7 (1992), Berzowsky for HIV-epitopes; The FASEB Journal 5:2412-2418 (1991).

Therefore, a first embodiment of the invention relates to vaccines for combating *Mycoplasma* infection, that comprise mycoplasmal L-α-glycerophosphate oxidase or an immunogenic fragment thereof, and a pharmaceutically acceptable carrier.

Such vaccines based upon the expression products of these genes can easily be made by admixing mycoplasmal L-α-glycerophosphate oxidase or an immunogenic fragment thereof with a pharmaceutically acceptable carrier as described below.

Another embodiment of the present invention relates to mycoplasmal L-α-glycerophosphate oxidase or an immunogenic fragment thereof for use in a vaccine.

Still another embodiment relates to the use of mycoplasmal L-α-glycerophosphate oxidase or an immunogenic fragment thereof for the manufacturing of a vaccine for combating *Mycoplasma* infections.

Another very attractive approach for vaccination against mycoplasmal infection is by using Live Recombinant Carriers (LRCs) comprising a gene or a fragment thereof encoding mycoplasmal L-α-glycerophosphate oxidase or an immunogenic fragment thereof, together with a pharmaceutically acceptable carrier. These LRCs are micro-organisms or viruses in which additional genetic information, in this case a gene or a fragment thereof encoding mycoplasmal L-α-glycerophosphate oxidase or an immunogenic fragment thereof, has been cloned. Animals infected with such LRCs will produce an immunogenic response not only against the immunogens of the carrier, but also against the immunogenic parts of the protein(s) for which the genetic code is additionally cloned into the LRC, e.g. mycoplasmal L-α-glycerophosphate oxidase. As an example of bacterial LRCs, attenuated *Salmonella* strains known in the art can attractively be used.

Live recombinant carrier parasites have i.a. been described by Vermeulen, A. N. (Int. Journ. Parasitol. 28: 1121-1130 (1998))

Also, LRC viruses may be used as a way of transporting the nucleic acid into a target cell. Live recombinant carrier viruses are also called vector viruses. Viruses often used as vectors are Vaccinia viruses (Panicali et al; Proc. Natl. Acad. Sci. US A, 79: 4927 (1982), Herpesviruses (E.P.A. 0473210A2), and Retroviruses (Valerio, D. et al; in Baum, S. J., Dicke, K. A., Lotzova, E. and Pluznik, D. H. (Eds.), Experimental Haematology today—1988. Springer Verlag, New York: pp. 92-99 (1989)).

The technique of in vivo homologous recombination, well-known in the art, can be used to introduce a recombinant nucleic acid into the genome of a bacterium, parasite or virus of choice, capable of inducing expression of the inserted nucleic acid according to the invention in the host animal.

Thus, still another embodiment of the present invention relates to vaccines for combating *Mycoplasma* infection that comprise a live recombinant carrier encoding mycoplasmal L-α-glycerophosphate oxidase or an immunogenic fragment thereof, and a pharmaceutically acceptable carrier.

It is clear that host cells comprising a gene or a fragment thereof encoding mycoplasmal L-α-glycerophosphate oxidase or an immunogenic fragment thereof under the control of a functionally linked promoter can be used for the production of the enzyme. There is no need to first extract the enzyme from the host cell before using it as a vaccine: the host cell can also be used as such. The same is true in case a host cell comprises an LRC expressing the enzyme. Examples thereof are eukaryotic cells comprising a viral or bacterial LRC.

Therefore, again another embodiment of the invention relates to a host cell comprising a gene or a fragment thereof encoding mycoplasmal L-α-glycerophosphate oxidase or an immunogenic fragment thereof under the control of a functionally linked promoter. This form also relates to a host cell containing a live recombinant carrier comprising a gene or a fragment thereof encoding mycoplasmal L-α-glycerophosphate oxidase or an immunogenic fragment thereof.

A host cell may be a cell of bacterial origin, e.g. *Escherichia coli, Bacillus subtilis* and *Lactobacillus* species, in combination with bacteria-based plasmids as pBR322, or bacterial expression vectors as pGEX, or with bacteriophages. The host cell may also be of eukaryotic origin, e.g. yeast-cells in combination with yeast-specific vector molecules, or higher eukaryotic cells like insect cells (Luckow et al; Bio-technology 6: 47-55 (1988)) in combination with vectors or recombinant baculoviruses, plant cells in combination with e.g. Ti-plasmid based vectors or plant viral vectors (Barton, K. A. et al; Cell 32: 1033 (1983), mammalian cells like Hela cells, Chinese Hamster Ovary cells (CHO) or Crandell Feline Kidney-cells, also with appropriate vectors or recombinant viruses.

Vaccines according to the invention based upon live recombinant carriers as described above, capable of expressing the enzyme or immunogenic fragments thereof e.g. based upon a *Salmonella* carrier or a viral carrier infecting the enteric epithelium, or e.g. the respiratory epithelium have the advantage over subunit vaccines that they better mimic the natural way of infection of *Mycoplasma*. Moreover, their self-propagation is an advantage since only low amounts of the recombinant carrier are necessary for immunisation.

An alternative and efficient way of vaccination is direct vaccination with DNA encoding the relevant antigen. Direct vaccination with DNA encoding proteins has been successful for many different proteins. (As reviewed in e.g. Donnelly et al., The Immunologist 2: 20-26 (1993)).

This way of vaccination is also very attractive for the vaccination of mammals against *Mycoplasma* infection.

Therefore, still another form of this embodiment of the invention relate s to a vaccine for combating *Mycoplasma* infection, that comprises a gene encoding mycoplasmal L-α-glycerophosphate oxidase or a part of said gene encoding an immunogenic fragment thereof, under the control of a functionally linked promoter and a pharmaceutically acceptable carrier.

DNA vaccines can easily be administered through intradermal application e.g. using a needle-less injector. This way of administration delivers the DNA directly into the cells of the animal to be vaccinated. Amounts of DNA in the microgram range between 1 and 100 μg provide very good results.

Vaccines described above all contribute to active vaccination, i.e. the host's immune system is triggered by the enzyme or an immunogenic fragment thereof, to make antibodies against these proteins.

Alternatively, such antibodies can be raised in e.g. rabbits or can be obtained from antibody-producing cell lines as described below. Such antibodies can then be administered to the host animal. This method of vaccination, passive vaccination, is the vaccination of choice when an animal is already infected, and there is no time to allow the natural immune response to be triggered. It is also the preferred method for vaccinating immune-compromised animals. Administered antibodies against *Mycoplasma* can in these cases bind directly to the bacteria. This has the advantage that it immediately decreases or stops *Mycoplasma* growth.

Therefore, one other form of this embodiment of the invention relates to vaccines comprising antibodies against mycoplasmal L-α-glycerophosphate oxidase or an immunogenic fragment thereof and a pharmaceutically acceptable carrier.

In still another form of this embodiment, the vaccine according to the present invention additionally comprises one or more antigens derived from other organisms or viruses that are pathogenic to the same host, antibodies against such antigens or genetic information encoding such antigens.

It goes without saying that a preferred combination vaccine is a vaccine comprising, next to mycoplasmal L-α-glycerophosphate oxidase, a *Mycoplasma* whole cell preparation. Such a combination vaccine would induce protection against not only the detrimental effects of mycoplasmal L-α-glycerophosphate oxidase, but also against other *Mycoplasma*-related proteins.

In case a *Mycoplasma* vaccine for the protection against a pig pathogenic *Mycoplasma* species is made, such organisms and viruses are preferably selected from the group of Pseudorabies virus, Porcine influenza virus, Porcine parvo virus, Transmissible gastro-enteritis virus, Rotavirus, another *Mycoplasma* spp., in particular, *Mycoplasma hyopneumoniae, Brachyspira hyodysenteriae, Escherichia coli, Leptospira* spp., *Erysipelothrix rhusiopathiae, Bordetella bronchiseptica, Brachyspira hyodysenteriae, Shigella* sp., *Salmonella choleraesuis, Salmonella typhimurium, Salmonella enteritidis, Haemophilus parasui,s Lawsonia, Pasteurella multocida, Streptococcus suis, Actinobacillus pleuropneumoniae, Staphylococcus hyicus* and *Clostridium perfringens*.

In case a *Mycoplasma* vaccine for the protection against a bovine pathogenic *Mycoplasma* species is made, such organisms and viruses are preferably selected from the group of Bovine Herpesvirus, bovine Viral Diarrhoea virus, Parainfluenza type 3 virus, Bovine Paramyxovirus, Foot and Mouth Disease virus, Bovine Respiratory Syncytial Virus, porcine circo virus, porcine respiratory reproductive syndrome virus, another *Mycoplasma* spp., *Pasteurella haemolytica, Staphylococcus aureus, Escherichia coli, Leptospira* spp., *Staphylococcus uberis, Theileria parva, Theileria annulata, Babesia bovis, Babesia bigemina, Babesia major, Trypanosoma* species, *Anaplasma marginale, Anaplasma centrale* and *Neospora caninum*.

In case a *Mycoplasma* vaccine for the protection against a poultry pathogenic *Mycoplasma* species is made, such organisms and viruses are preferably selected from the group of Fowlpox virus, Infectious Bronchitis virus, Infectious Bursal Disease (Gumboro), Marek's Disease Virus, Chicken Anaemia agent, Avian Reovirus, Turkey Rhinotracheitis virus, Chicken Poxvirus, Avian Encephalomyelitisvirus, Duck Plague virus, Newcastle Disease virus, Egg prop syndrome virus, Infectious Laryngotracheitis virus, Herpes Virus of Turkeys, another *Mycoplasma* spp. i.a. *Mycoplasma gallisepticum* or *Mycoplasma synoviae, Haemophilus paragallinarum* (Coryza), *Ornithobacterium rhinotracheale, Clostridium perfringens, Salmonella* species, *Campylobacter* species, *E. coli* and *Eimeria* species.

In case a *Mycoplasma* vaccine for the protection against a human pathogenic *Mycoplasma* species is made, such organisms and viruses are preferably selected from the group of influenza virus, measles virus, mumps paramyxovirus, *Clostridium diphteriae, Clostridium tetani, Bordetella pertussis*, another *Mycoplasma* spp. and pox virus.

Preferably, the mycoplasmal L-α-glycerophosphate oxidase or an immunogenic fragment thereof, as mentioned above is the mycoplasmal L-α-glycerophosphate oxidase as encoded by any of the following mycoplasmas: *M. bovis, M. sp.bovine group 7, M. mycoides* subsp. *Capri, M. penetrans, M. gallisepticum, M. synoviae, M. mobile, M. pulmonis, M. hyopneumoniae, M. pneumoniae, M. genitalium, M. mycoides* S(mall) C(olony) strain Afadé or *M. mycoides* S(mall) C(olony) strain L2, in particular, *M. bovis, M. hyopneumoniae, M. gallisepticum* or *M. synoviae*, more in particular, *M. bovis* or *M. hyopneumoniae*.

All vaccines according to the present invention comprise a pharmaceutically acceptable carrier. A pharmaceutically acceptable carrier can be e.g. sterile water or a sterile physiological salt solution. In a more complex form the carrier can e.g. be a buffer.

Methods for the preparation of a vaccine comprise the admixing of mycoplasmal L-α-glycerophosphate oxidase or an immunogenic fragment thereof, a live recombinant carrier as described above, a gene or a part thereof as described above, a host cell as described above or antibodies against mycoplasmal L-α-glycerophosphate oxidase or an immunogenic fragment thereof, and a pharmaceutically acceptable carrier. Therefore, another embodiment of the present invention relates to a method for the preparation of a vaccine for combating *Mycoplasma* infection which method comprises the admixing of mycoplasmal L-α-glycerophosphate oxidase or an immunogenic fragment thereof as described above, a live recombinant carrier as described above, a gene or a part thereof as described above, a host cell as described above or antibodies against mycoplasmal L-α-glycerophosphate oxidase or an immunogenic fragment thereof as described above, and a pharmaceutically acceptable carrier.

Vaccines according to the present invention may in a preferred presentation also contain an adjuvant. Adjuvants in general comprise substances that boost the immune response of the host in a non-specific manner. A number of different adjuvants are known in the art. Examples of adjuvants are Freunds Complete and Incomplete adjuvant, vitamin E, non-ionic block polymers, muramyldipeptides, QuillA®, mineral oil e.g. Bayol® or Markol®, vegetable oil, and Carbopol® (a homopolymer), or Diluvac® Forte. The vaccine may also comprise a so-called "vehicle". A vehicle is a compound to which the polypeptide adheres, without being covalently bound to it. Often used vehicle compounds are e.g. aluminium hydroxide, -phosphate or -oxide, silica, Kaolin, and Bentonite.

A special form of such a vehicle, in which the antigen is partially embedded in the vehicle, is the so-called ISCOM (EP 109.942, EP 180.564, EP 242.380)

In addition, the vaccine may comprise one or more suitable surface-active compounds or emulsifiers, e.g. Span or Tween.

Often, the vaccine is mixed with stabilisers, e.g. to protect degradation-prone polypeptides from being degraded, to enhance the shelf-life of the vaccine, or to improve freeze-drying efficiency. Useful stabilisers are i.a. SPGA (Bovarnik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates.

In addition, the vaccine may be suspended in a physiologically acceptable diluent. It goes without saying, that other ways of adjuvating, adding vehicle compounds or diluents, emulsifying or stabilising a polypeptide are also embodied in the present invention.

Vaccines according to the invention can very suitably be administered in amounts ranging between 1 and 100 micrograms of proteins, although smaller doses can in principle be used. A dose exceeding 100 micrograms will, although immunologically very suitable, be less attractive for commercial reasons.

Vaccines based upon live attenuated recombinant carriers, such as the LRC-viruses and bacteria described above can be administered in much lower doses, because they multiply themselves during the infection. Therefore, very suitable amounts would range between $10^3$ and $10^9$ CFU/PFU for respectively bacteria and viruses.

Many ways of administration can be applied. Oral application is a very attractive way of administration, because it is not labour-intensive. A preferred way of oral administration is the packaging of the vaccine in capsules, known and frequently used in the art, that only disintegrate after they have passed the highly acidic environment of the stomach. Also, the vaccine could be mixed with compounds known in the art for temporarily enhancing the pH of the stomach.

Systemic application is also suitable, e.g. by intramuscular application of the vaccine. If this route is followed, standard procedures known in the art for systemic application are well-suited.

Vaccines based upon mycoplasmal L-α-glycerophosphate oxidase are also very suitable as marker vaccines. A marker vaccine is a vaccine that allows to discriminate between vaccinated and field-infected animals e.g. on the basis of a characteristic antibody panel, different from the antibody panel induced by wild type infection.

A vaccine based upon purified mycoplasmal L-α-glycerophosphate oxidase would only induce antibodies against that protein, whereas a vaccine based upon a live wild-type, live attenuated or inactivated whole *Mycoplasma*, as well as field infection would induce antibodies against all or most of the bacterial proteins: this would clearly give a highly different antibody panel.

A simple ELISA test, having wells comprising purified mycoplasmal L-α-glycerophosphate oxidase and wells comprising another mycoplasmal protein suffices to test serum from animals and to tell if the animals are either vaccinated with a vaccine according to the invention or suffered from *Mycoplasma* field infection; animals vaccinated with a vaccine comprising purified mycoplasmal L-α-glycerophosphate oxidase would not have antibodies against other mycoplasmal proteins than the mycoplasmal L-α-glycerophosphate oxidase. Animals that have encountered a field infection with *Mycoplasma* would however have antibodies against all immunogenic Mycoplasma proteins and thus also against other, non mycoplasmal L-α-glycerophosphate oxidase protein.

Thus, another embodiment of the present invention relates to a diagnostic test for the discrimination between vaccination with a vaccine according to the invention on the one hand and vaccination with a whole cell vaccine or a field infection on the other hand, wherein such a test comprises purified mycoplasmal L-α-glycerophosphate oxidase or an immunogenic fragment thereof and separately another, non-L-α-glycerophosphate oxidase protein.

The polypeptides or immunogenic fragments thereof according to the invention expressed as characterised above can be used to produce antibodies, which may be polyclonal, monospecific or monoclonal (or derivatives thereof). If polyclonal antibodies are desired, techniques for producing and processing polyclonal sera are well-known in the art (e.g. Mayer and Walter, eds. *Immunochemical Methods in Cell and Molecular Biology*, Academic Press, London, 1987).

Monoclonal antibodies, reactive against the polypeptide according to the invention (or variants or fragments thereof) according to the present invention, can be prepared by immunising inbred mice by techniques also known in the art (Kohler and Milstein, *Nature*, 256, 495-497, 1975).

Methods for large-scale production of antibodies according to the invention are also known in the art. Such methods rely on the cloning of (fragments of) the genetic information encoding the protein according to the invention in a filamentous phage for phage display. Such techniques are described in review papers by Cortese, R. et al., (1994) in Trends Biotechn. 12: 262-267., by Clackson, T. & Wells, J. A. (1994) in Trends Biotechn. 12: 173-183, by Marks, J. D., et al., (1992) in J. Biol. Chem. 267: 16007-16010, by Winter, G. et al., (1994) in Annu. Rev. Immunol. 12: 433-455, and by Little, M. et al., (1994) Biotechn. Adv. 12:539-555. The phages are subsequently used to screen camelid expression libraries expressing camelid heavy chain antibodies. (Muyldermans, S, and Lauwereys, M., Journ. Molec. Recogn. 12: 131-140 (1999) and Ghahroudi, M. A. et al., FEBS Letters 414:%12-526 (1997)). Cells from the library that express the desired antibodies can be replicated and subsequently be used for large scale expression of antibodies.

EXAMPLES

Example 1

Strains, Cells, Growth Conditions and DNA Extraction

*M. mycoides* subsp. *mycoides* SC strain Afadé, a highly virulent field strain isolated in 1968 at Farcha Laboratory, N'Dj aména, Chad, was used for the virulence studies unless marked specifically. This strain causes CBPP under natural and experimental conditions. A less virulent strain, *M. mycoides* subsp. *mycoides* SC strain L2, which lacks the active glycerol uptake system G tsABC, has been used where stated specifically. Furthermore, the type strain PG1 and ten other strains from African and European outbreaks were also used in this study for genetic analyses. Mycoplasmal cultures were grown in mycoplasma broth medium to a density of $10^8$-$10^9$ colony forming units/ml (cfu/ml) or on solid mycoplasma agar medium (Axcell Biotechnologies, St. Genis l'Argentiére, France). Growth and handling of live *M. mycoides* subsp. *mycoides* SC was performed in a biological safety laboratory fulfilling the BL3 containment safety standards. DNA extraction was performed as previously described (Cheng, X., J. et al., 1995, Microbiology 141: 3221-3228). For genetic manipulation and sub-cloning, *Escherichia coli* strains DH5 α [F⁻φ80dlacZΔM15 Δ(lac-ZYA-argF) U169 deoR recA1 endA1 hsdR17($r_K^-$, $m_K^+$)phoA supE44 λ⁻thi-1 gyrA96 relA1] and BL21(DE3) [F' dcm ompT hsdS($r_B^-$ $m_B^-$) gal λ(DE3)] were used. The pETHIS-1 expression vector (Schaller, A. et al., 1999, Microbiology 145: 2105-2116) was used for expression of recombinant poly-histidine N- and C-terminal fusion proteins.

ECaNEp cells were prepared from fetuses obtained from a local abattoir, and were maintained in MEM-Earle media supplemented with 7% fetal calf serum (FCS) and penicillin (100 IU/ml) in 24-well microtiter plates and used at confluent density of $2 \times 10^5$ cells per well, at 37° C. in a humidified 5% $CO_2$ atmosphere. FCS and cell culture media were purchased from Seromed (Biochrom, Munich, Germany). Cells were routinely screened for contamination by mycoplasmas using PCR or by BVD virus using immunostaining.

PCR Amplification, Southern Blot and DNA Sequence Analysis.

A glpO specific DNA probe was constructed by PCR in the presence of digoxigenin-11-dUTP (Dig) (Roche Diagnostics, Rotkreuz, Switzerland) using the oligonucleotide primers glpO EcoRI N (5'-TCGAATTCAAGCAAACAAAAGT-TGATATTTG -3") [SEQ ID NO.:2] and glpO NotI C(5'-TTGCGGCCGCATTTCCATGGAAGAATAGCTTCTTC -3') [SEQ ID NO.: 1] using standard PCV conditions (Cheng, X., et al., 1995, Microbiology 141: 3221-3228). Extraction of genomic DNA from mycoplasmas and Southern blot analysis were performed as previously described (Pilo, P. et al., 2003, Vet. Microbiol. 92: 37-48).

DNA sequencing was performed with a DNA Sequenator AB 3100 genetic analyzer and the Taq dye deoxy terminator cycle sequencing kit (Applied Biosystems, Norwalk, Conn.), with oligonucleotide primers glpO EcoRI N and glpO NotI C and by primer walking using glpO internal primers. The DNA and deduced amino acid sequences were analyzed with the PC/Gene program PROSITE (Bairoch, A., P. Bucher and K. Hoffman. 1995, Nucleic Acids Res. 24: 189-196). Sequence comparisons with GenBank and EMBL databases were performed using BLAST (Altschul, S. F., et al., 1997, Nucleic Acids Res. 25:3389-3402). Analysis of proteins was carried out by using programs Motif Scan and TMpred. and the "toppred" software (von Heijne, G. 1992, J. Mol. Biol. 225: 487-494.).

Example 2

Cloning, Site-Directed Mutagenesis and Expression of Recombinant GlpO

The glpO gene of *M. mycoides* subsp. *mycoides* SC strain Afadé was first amplified with the primers glpO_EcoRI_N and glpO_NotI_C containing the restriction sites for EcoRI and NotI, respectively. Furthermore, primer glpO_NotI_C included a mutated $TGG_{Trp}$ codon. The other two mycoplasma-specific $TGA_{Trp}$ codons in the glpO gene were replaced with $TGG_{Trp}$ codons, using the overlap extension-PCR method (Braman, J., C. Papworth, and A. Greener. 1996, Methods Mol. Biol. 57: 31-44.) with the primer pairs (carrying the appropriate nucleotide substitutions) glpO_mut1L (5'-GAAGACTGGATCAAAGAAATGGA-3') [SEQ ID NO.: 6]/glpO_mut1R (5'-TTTGATCCAGTCTTCAT-AACGTTT-3') [SEQ ID NO.: 5] or glpO_mut2L (5'-GCTAATTGGCAACCAAAAGAAGA-3') [SEQ ID NO.: 4]/glpO_mut2R (5"-TGGTTGCCAATTAGCCTTTTTATC-3') [SEQ ID NO.: 3]. The PCR product was cloned into pETHIS-1 by flanking EcoRI and NotI cleavage sites. The construct was analyzed by DNA sequencing and introduced into E. cili BL21(DE3) for expression and purification via $Ni^{2+}$-chelation chromatography of the polyhistadine—tailed fusion protein as described previously for other proteins (Schaller, A., et al., 1999, Microbiology 145: 2105-2116).

Example 3

Sera, Polyclonal Antibodies, Immunoglobulin Purification and Fab Preparation

Bovine sera from a controlled experimental infection with the African *M. mycoides* subsp. *mycoides* SC strain Afadé have been described in detail by Abdo and colleagues (Abdo, E.-M. et al., 1998, Vet. Microbiol. 59: 109-122.). Polyclonal monospecific serum directed against recombinant GlpO was obtained by subcutaneous immunization of rabbits with 160 µg of purified recombinant polyhistidine-tailed protein GlpO in 500 µl of PBS buffer pH 8.0 (50 mM $Na_2HPO_4/NaH_2PO_4$ pH 8.0, 140 mM NaCl) mixed with 500 µl of Adjuvant 10 (Gerbu Biotechnik GmbH, Gaiberg, Germany), followed by booster immunizations with 40 and 20 µg of protein at 2 and 4 weeks. The rabbits were bled 10 days after the last booster immunization. Antisera were prepared from the blood samples and stored at −20° C.

Immunoglobulin G (IgG) fractions from rabbit anti-GlpO serum and from pre-serum of the same rabbit were purified with the HiTrap Protein G kit (Amersham Pharmacia Biotech, Uppsala, Sweden) as directed by the manufacturer. Preparation of Fab fragments was performed with the ImmunoPure Fab Preparation kit (Pierce, Rockford, Ill.) according to the manufacturer's instruction. Fab fragments were dialyzed overnight against PBS buffer pH 7.4 and then filter-sterilized. Protein concentrations were determined using the method of Bradford (Bradford, M. M. 1976, Anal. Biochem. 72: 248-254.). Monospecific rabbit serum directed against lipoprotein LppC has been previously described (Pilo, P. et al., 2003, Vet. Res. 34: 761-775.).

Example 4

Immunoblot Analysis, Triton X-114 Partitioning and Growth Inhibition Test

Total antigens from mycoplasmas were prepared as previously described (Fleury, B. et al, 2001, J. Clin. Microbiol. 39:2814-2822). Immunoblotting was carried out with bovine serum at a dilution of 1:2000 and rabbit monospecific serum anti-GlpO at a dilution of 1:1000.

*M. mycoides* subsp. *mycoides* SC total antigen from a stationary phase culture was separated into hydrophobic and hydrophilic fractions by the Triton X-114 partitioning method (Bordier, C. 1981, J. Biol. Chem. 256: 1604-1607). Samples from the Triton X-114 detergent phase and the aqueous phase were analyzed by immunoblotting with the monospecific, polyclonal antibodies directed agains t GlpO and with the bovine serum directed against *M. mycoides* subsp. *mycoides* SC.

The growth inhibition tests were performed by spotting 5 and 10 µl of undiluted, decomplemented monospecific rabbit serum against GlpO, purified IgG or Fab fragments of anti-GlpO IgG onto the mycoplasma-containing agar medium and incubating the plates at 37° C. for 4 days. Serum against *M. mycoides* subsp. *mycoides* SC was used as positive control, and monospecific rabbit serum against LppQ as negative control. Observation of growth inhibition was carried out under a light microscope as previously described (Papazisi, L. et al, 2003, Microbiology 149: 2307-2316, Poveda, J. B., and R. Nicholas, 1998, Methods Mol. Biol. 104: 105-111.).

Example 5

Scanning Electron Microscopy (SEM) and Immunogold Labelling

For electron microscopy, *M. mycoides* subsp. *mycoides* SC were cultured at 37° C. for 5 days in mycoplasma broth medium on gold or platinum-sputtered coverslips that had been pre-coated with poly-L-lysine. Cells were washed three times with PBS buffer pH 7.4 at 37° C. and fixed in 4% paraformaldehyde in PBS for 30 min at room temperature. After washing with PBS, the coverslips were blocked in PBS buffer supplemented with 0.2 M glycine and 1% BSA for 15 min at room temperature, and thereafter they were incubated with IgG from rabbit serum anti-GlpO diluted 1:100 or 1:50 in PBS supplemented with 1% BSA overnight at 4° C. Samples were then washed with PBS for 10 min and labelled with 15 nm colloidal gold-conjugated goat anti-rabbit IgG (British Biocell International, Cardiff, UK) diluted 1:50 in PBS for 90 min at room tempearture. Coverslips were washed with 0.1 M cacodylate buffer pH 7.4 and processed for SEM following standard protocols. Briefly, samples were osmicated in 1.33% $OsO_4$ with 0.11% ruthenium red in 0.13 M cacodylate buffer pH 7.4 for 15 min, washed with 0.1 M cacodylate buffer, dehydrated through an ascending ethanol series, and dried by evaporation of hexamethyldisilazane (Sigma, Buchs, Switzerland).

Secondary electron and corresponding backscattered electron signals were examined in a high-resolution field emission scanning electron microscope DSM 982 Gemini (Zeiss, Oberkochen, Germany) at an accelerating voltage of 5 kV, a working distance of 8 mm and a magnification from 50,000 to 100,000 X.

Control experiments included omission of primary antibody as well as the use of a rabbit anti-calcitonine antibody (Anawa Biomedical Services and Products, Zurich Switzerland) and of rabbit pre-immune serum, respectively.

Example 6

Quantification of $H_2O_2$ Production and Inhibition Assay

To measure $H_2O_2$ production, strains of *M. mycoides* subsp. *mycoides* SC were grown in mycoplasma culture medium for 3 days at 37° C. to a density of approximately $5 \times 10^8$ cfu/ml. The culture was centrifuged at 80 000×g for 10 min at 4° C., washed once in incubation medium (67.6 mM HEPES pH 7.3, 140 mM NaCl, 7 mM $MgCl_2$), re-suspended in pre-warmed incubation medium at 37° C. at a density of $10^9$ cfu/ml, portioned in aliquots of 1 ml and incubated at 37° C. for 1 hour. To induce $H_2O_2$ production, glycerol was added to the mycoplasma suspensions at a final concentration of 100 µM, the physiological concentration in bovine serum. The production of $H_2O_2$ was measured with the peroxide test (Merck KgaA, Darmstadt, Germany) as described previously (Vilei, E. M., and J. Frey, 2001, Clin. Diagn. Lab. Immunol. 8: 85-92.) 0, 1, 2, 5, 10, 20 and 120 min after the addition of glycerol. In order to inhibit the mycoplasmal L-α-glycerolphosphate oxidase GlpO, mycoplasmas were pre-treated with purified Fab fragments of IgG directed against GlpO by incubation at concentrations from 0.26 µg/ml to 2.6 µg/ml followed by two washes with PBS buffer. To assess the viability of *M. mycoides* subsp. *mycoides* SC cells after induction of $H_2O_2$ production, aliquots of the reaction assays were plated on mycoplasma agar plates at the end of the assay and grown at 37° C.

Example 7

Assessment of Cytotoxic Activity

Embryonic calf nasal epithelial cells (ECaNEp cells) (Schweizer, M., and E. Peterhans, 1999, J. Gen. Virol. 80: 1147-1155.) were grown in 24-well plates until confluence was reached. Prior to the assay, the medium was removed and replaced by 200 µl of MEM-Earle medium without supplements, or by MEM-Earle medium supplemented with 100 M glycerol. The ECaNEp cells were then infected at a multiplicity of infection (MOI) of 50 mycoplasmas per cell. To block the GlpO activity, *M. mycoides* subsp. *mycoides* SC were pre-treated with anti-GlpO Fab fragments at 0.26 µg/ml. Viable ECaNEp cells were counted after fixation and staining with 0.75% crystal violet, 0.25% NaCl, 1.75% formaldehyde and 50% ethanol and photographed under phase contrast microscopy at various times after infection. Purified Fab fragments from polyclonal IgG directed against the membrane lipoprotein LppC of *M. mycoides* subsp. *mycoides* SC were used as a control since LppC is not correlated to the glycerol metabolism. In order to determine whether $H_2O_2$ produced during growth of *M. mycoides* subsp. *mycoides* SC prior to contact with ECaNEp cells would be deleterious to the bovine cells, supernatant of cultures of *M. mycoides* subsp. *mycoides* SC grown in presence of glycerol was filtered through a 0.22-µm filter (Millipore, Bedford, Mass.) and added to ECaNEp cells. The ECaNEp cell viability was assessed by trypan blue exclusion.

Example 8

Detection of Oxidative Stress Caused by $H_2O_2$ and other ROS in ECaNEp Cells

The oxidation of 5 (and 6)-chloromethyl-2',7'-dichlorodihydrofluorescein diacetate-acetyl ester (CM-$H_2$DCFDA; Molecular Probes, Eugene, Oreg.) was used to assess oxidative stress by intracellular ROS in ECaNEp cells. This dye enters the cells and produces a fluorescent signal after intracellular oxidation by ROS. The same conditions used for the assessment of cytotoxic activity were employed with the following modifications. As controls, half of the wells containing ECaNEp cells were treated with 30 mM N-acetyl-L-cysteine (NAC) to prevent oxidation by $H_2O_2$ and ROS. Then, the ECaNEp cells were incubated for 1 hour with 10 µM CM-$H_2$DCFDA and washed once with MEM-Earle medium. Cells were then infected at a MOI of 500 mycoplasmas per cell in presence or absence of glycerol. To block the GlpO activity, *M. mycoides* subsp. *mycoides* SC were pre-treated with anti-GlpO Fab fragments at 0.26 µg/ml. As a control, cells were treated with $H_2O_2$ solutions ranging from 150 µM to 4.4 mM for 20 min. Intracellular $H_2O_2$ and ROS was monitored 20 min after infection with mycoplasmas by fluorescence microscopy using a Nikon Eclipse TE 300 microscope. Note that all steps involving CM-$H_2$DCFDA, including handling of this chemical, were performed in the dark.

Nucleotide Sequence Accession Numbers.

The EMBL/GenBank accession numbers for the nucleotide sequences of glpO from *M. mycoides* subsp. *mycoides* SC strains Afadé and L2 are AJ581566 and AJ581564, respectively. The sequences of the glpO genes from *Mycoplasma* sp. bovine group 7 strain PG50 and *M. mycoides* subsp. *capri* strain PG3 have been deposited under accession numbers AJ581565 and AJ581567, respectively.

Example 9

Genetic and Functional Analysis of the glpO Gene

The glpO gene from *M. mycoides* subsp. *mycoides* SC encodes a 387-aa polypeptide, GlpO, with a predicted molecular mass of 42.7 kDa and a pI of 8.14. It contains three TGATP codons. The protein has a putative FAD-binding site at amino acid positions 8 to 36 and appears to be surface-exposed. TMpred identified two significant transmembrane regions, spanning amino acids 6 to 25 and 140 to 157. The glpO gene is followed by the genes glpK (putative glycerol phosphate kinase) and glpF (putative glycerol facilitator factor) in the highly virulent strain Afadé. The same gene arrangement is observed for to the type strain PG1. Southern blot analysis of genomic DNA with the gene probe for glpO showed the presence of glpO in *M. mycoides* subsp. *mycoides* SC strains Afadé, L2, the type strain PG1 and in ten other strains from African and European outbreaks that were analyzed (data not shown). Immunoblot analysis of total antigens with monospecific anti-GlpO IgG revealed a distinct 45-kDa protein band confirming the expression of the glpO gene in all strains of *M. mycoides* subsp. *mycoides* SC tested (data not shown). The amino acid sequence of GlpO from *M. mycoides* subsp. *mycoides* SC strain Afadé and strain L2 was found to be identical to that of the GlpO of the type strain PG1 (48) and showed similarity to the glycerol-3-phosphate dehydrogenases of various *Mycoplasma* species (Table 1).

Genome sequence analysis predicts that mycoplasmas are devoid of catalase and dismutase activities. Since cytoplasmic GlpO activity would induce intracellular $H_2O_2$ toxicity that in its turn would be deleterious to the mycoplasma itself, we hypothesized that the enzyme must be located at the surface membrane. Sequence analysis of GlpO or homologous enzymes from various pathogenic *Mycoplasma* species (listed in Table 1) using "toppred" software revealed transmembrane structures predicting domains of these enzymes to be surface-located. Direct evidence for the presence of GlpO at the cell surface of *M. mycoides* subsp. *mycoides* SC was provided by scanning electron microscopy (SEM) after immunogold labelling using IgG from monospecific rabbit anti-GlpO serum (FIG. 1a-d). To confirm the location of GlpO in the mycoplasmal membrane, total protein of *M. mycoides* subsp. *mycoides* SC was subjected to Triton X-114 phase partitioning. Anti-GlpO serum reacted strongly with a 45-kDa protein (GlpO) in the Triton X-114 phase, which was absent from the aqueous phase, indicating that GlpO is an integral membrane protein of *M. mycoides* subsp. *mycoides* SC (FIG. 1e). Immunoblot analysis of the Triton X-114 extract of *M. mycoides* subsp. *mycoides* SC with bovine serum from a cow that was experimentally infected with this strain revealed the GlpO-specific band at 45 kDa that co-migrated on the gel with GlpO (data not shown), showing that GlpO is involved in sero-conversion during CBPP infection of cattle.

In order to confirm the function of GlpO as a mycoplasmal L-α-glycerophosphate oxidase, we measured the production of $H_2O_2$ after the addition of glycerol to an axenic culture of *M. mycoides* subsp. *mycoides* SC in presence or absence of Fab fragments of monospecific anti-GlpO IgG. As shown in FIG. 1f, the addition of 100 µM glycerol to the culture at mid-exponential growth phase instantly resulted in the release of $H_2O_2$ into the growth medium reaching 150 µM after 10 minutes, a concentration that was retained up to 2 hours (FIG. 1f). The release of $H_2O_2$ could be blocked specifically when the mycoplasma suspensions were pre-treated with monospecific polyclonal anti-GlpO antibodies or Fab fragments of anti-GlpO IgG at a minimal concentration of 0.26 µg/ml but not by Fab fragments of anti-LppC IgG used as a control antibody (FIG. 1f). LppC is a surface lipoprotein of *M. mycoides* subsp. *mycoides* SC that is not related to the glycerol metabolism. The addition of catalase to the culture of *M. mycoides* subsp. *mycoides* SC after supplementation with glycerol reduced the $H_2O_2$ levels in the medium to a concentration below 1 µM, which is the detection level of the assay. The generation time of *M. mycoides* subsp. *mycoides* SC was 3.3 hours without or with the addition of anti-GlpO antibodies or anti-GlpO Fab fragments. Furthermore, anti-GlpO antibodies had no effect in the serum-drop growth inhibition tests (data not shown). An axenic culture that was grown in presence of 100 µM glycerol for 2 hours and that produced 150 µM $H_2O_2$ showed a generation time of 3.2 hours, while the control culture to which no glycerol was added had a generation time of 3.3 hours. Hence, the viability of mycoplasmas was not affected by the glycerol-induced production of $H_2O_2$.

Example 10

Figure 2:
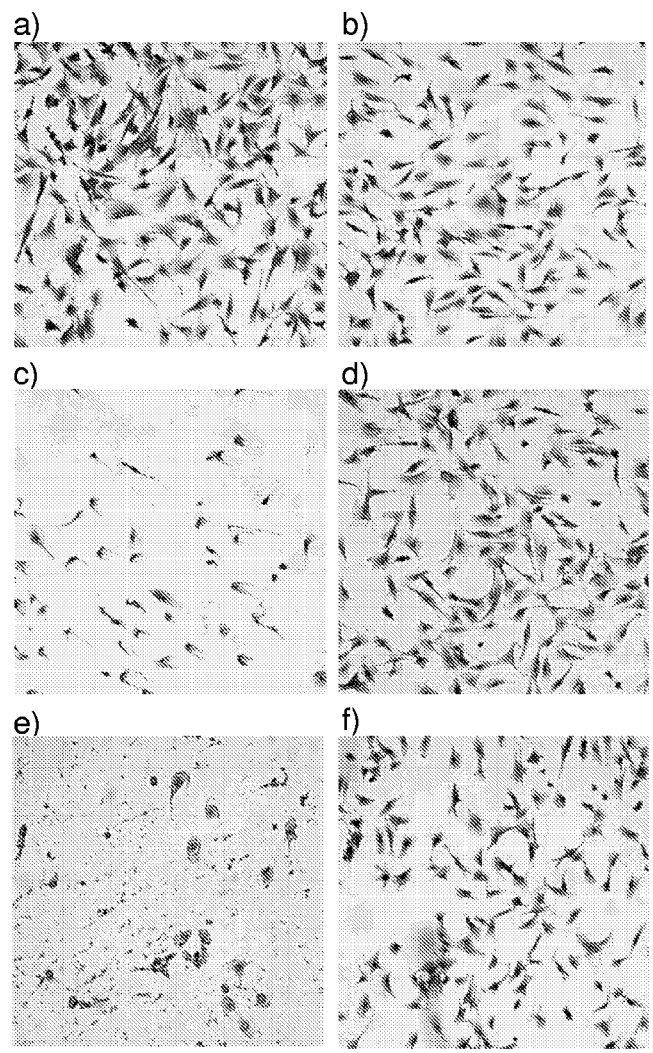
Figure 2:
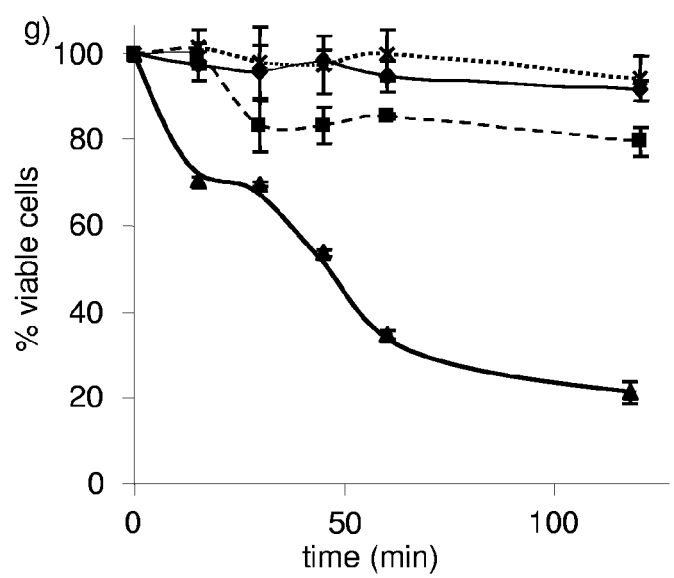

Cytotoxicity of *M. mycoides* subsp. *mycoides* SC Towards Bovine Epithelial Cells To assess whether the production of $H_2O_2$ and related ROS, resulting from glycerol metabolism, contributes to the virulence of *M. mycoides* subsp. *mycoides* SC, we analyzed the cytotoxicity towards embryonic calf nasal epithelial (ECaNEp) cells under various conditions (FIG. 2). As shown in FIG. 2b, infection of ECaNEp cells with *M. mycoides* subsp. *mycoides* SC strain Afadé at a MOI of 50 mycoplasmas per cell resulted in only a weak cytotoxic effect 1 hour post infection in the absence of glycerol in the culture medium. However, when the infection of the ECaNEp cells with the mycoplasma was made in presence of physiological concentrations of glycerol, most ECaNEp cells detached from the surface and subsequently underwent complete lysis (FIG. 2c). This cytotoxic effect could be blocked when the mycoplasmas were pre-treated with anti-GlpO Fab fragments at a concentration of 0.26 µg/ml, which concomitantly block $H_2O_2$ production. Under these conditions, the ECaNEp cells showed no morphological changes 1 hour post infection (FIG. 2d). The cytotoxicity of *M. mycoides* subsp. *mycoides* SC grown in glycerol-containing medium was not inhibited by anti-LppC Fab fragments that were used as a control (FIG. 2e). Only a weak cytotoxic effect was observed when ECaNEp cells were infected, in presence of glycerol, with a less virulent strain (L2) that lacks genes for the active glycerol transporter Gts ABC and produces only low amounts of $H_2O_2$ (FIG. 2f). In control experiments, the addition of glycerol, anti-GlpO Fab or anti-LppC Fab alone or in combination did not affect the ECaNEp cells (data not shown). The kinetics of cytotoxicity experiments (FIG. 2g) show that induction of cytotoxicity occurs rapidly after addition of glycerol to ECaNEp cells infected with *M. mycoides* subsp. *mycoides* SC, reaching 75% mortality after 2 hours. At a higher MOI (500 mycoplasmas per cell), full mortality of the cells was reached at 30 minutes after addition of glycerol. Pretreatment of mycoplasmas with anti-GlpO Fab fully prevented from cell mortality over the entire observation period (FIG. 2g). In the absence of added glycerol, infection of ECaNEp cells with *M. mycoides* subsp. *mycoides* SC shows only a weak cytotoxic effect (FIG. 2g), which could also be inhibited by anti-GlpO Fab and might therefore be due to residual amounts of glycerol in the cell or culture medium. Interestingly, filtered supernatant of *M. mycoides* subsp. *mycoides* SC cultures grown in the presence of glycerol, containing approximately 150 µM $H_2O_2$, or the addition of 150 µM $H_2O_2$ to the cell cultures had no visible cytotoxic effect on ECaNEp cells after 1-hour exposure. Cytotoxicity induced by addition of exogenous $H_2O_2$ to ECaNEp cell cultures was first reached at a concentration of 4.4 mM with most of the cells dying after 1 hour of exposure. This concentration is 30 times higher than that measured in growth medium of *M. mycoides* subsp. *mycoides* SC in presence of glycerol.

Figure 3:
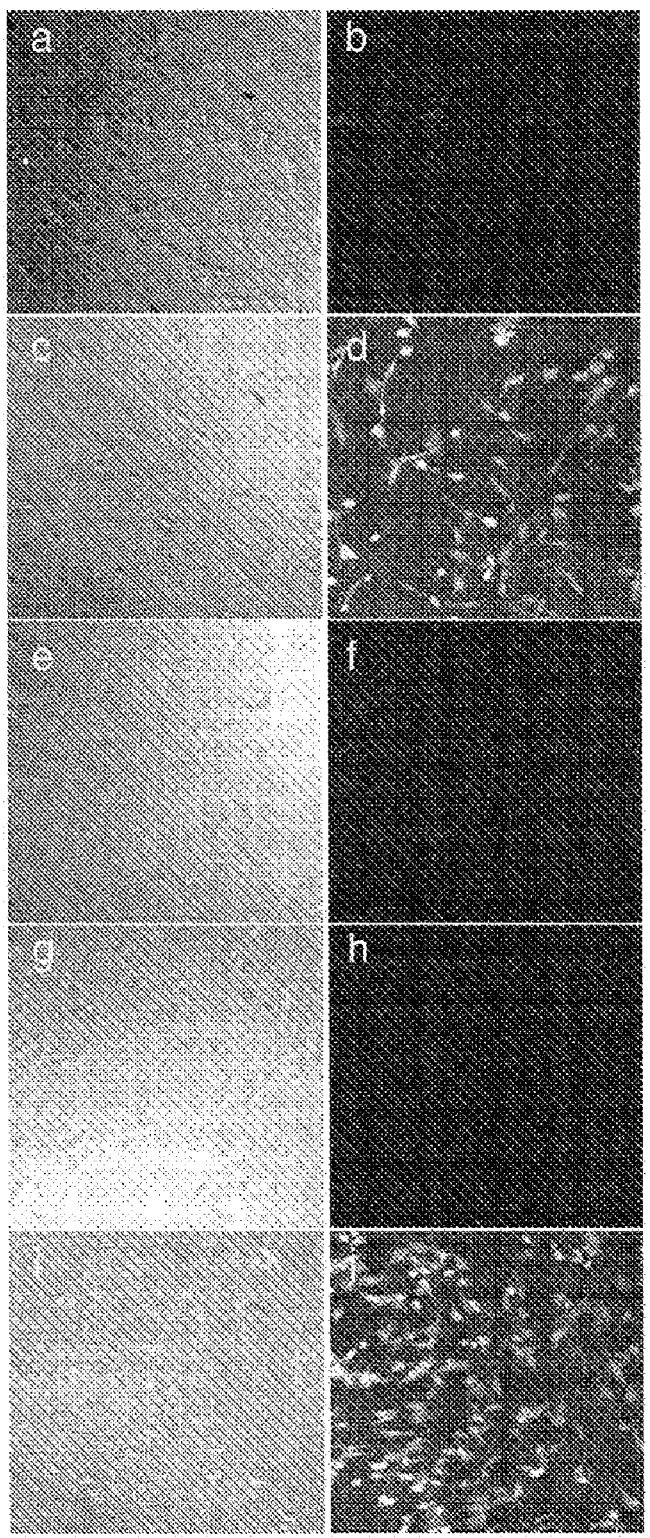

To monitor oxidative stress in the ECaNEp cells caused by intracellular $H_2O_2$ and other ROS after infection with *M. mycoides* subsp. *mycoides* SC or addition of glycerol, we pre-treated ECaNEp cells with CM-$H_2$DCFDA and detected intracellular oxidation of this compound by fluorescence microscopy (FIG. 3). The cleavage of the ester groups by oxidation of CM-$H_2$DCFDA results in the formation of dichlorofluorescein (DCF) derivatives in the cells, which are highly fluorescent, while non-oxidized CM-H$_2$DCFDA is non-fluorescent. As shown in FIG. 3c-d, infection of ECaNEp cells with *M. mycoides* subsp. *mycoides* SC resulted in a strong induction of fluorescence in ECaNEp cells 20 min after addition of glycerol, reflecting the presence of intracellular H$_2$O$_2$ or ROS. In contrast, no fluorescence was detected in infected ECaNEp cells without the addition of glycerol (FIG. 3a-b). Intracellular oxidation of CM-H$_2$DCFDA did not occur when the mycoplasmas were treated with anti-GlpO antibodies prior to the infection of ECaNEp cells (FIG. 3c-f). Furthermore, intracellular oxidation of CM-H$_2$DCFDA was blocked by treating the ECaNEp cells with the antioxidant agent, NAC, prior to the addition of glycerol to the culture medium (FIG. 3g-h). Intracellular oxidation of ECaNEp cells did not occur upon addition of exogenous H$_2$O$_2$ at 150 µM, a concentration corresponding to that released by *M. mycoides* subsp. *mycoides* SC 10 min after addition of glycerol. As was the case for the induction of cytotoxicity, to achieve oxidation of intracellular CM-H$_2$DCFDA in ECaNEp cells, concentrations of 4.4 mM exogenous H$_2$O$_2$ were necessary (FIG. 3i-j).

CONCLUSION

In the present invention GlpO of *M. mycoides* subsp. *mycoides* SC has been identified as a membrane protein that plays a central role in cytotoxicity towards ECaNEp cells. In the presence of physiological concentrations of glycerol, *M. mycoides* subsp. *mycoides* SC at a density of $10^9$ cfu/ml releases relatively large amounts of H$_2$O$_2$, up to 150 µM into the culture medium. This amount of H$_2$O$_2$ is approximately twenty-fold if compared to that produced by mycoplasmas grown in presence of glucose, which was reported to stimulate H$_2$O$_2$ production by just 50%. When ECaNEp cells were exposed to *M. mycoides* subsp. *mycoides* SC, in presence of physiological concentrations of glycerol, H$_2$O$_2$ was first detected in their cytosol and, subsequently, cell death occurred. We noticed a marked discrepancy between the H$_2$O$_2$ concentration released by the mycoplasmas into the medium and that required to trigger CM-H$_2$DCFDA oxidation and cell death. Thus, filtered mycoplasmal growth medium containing 150 µM H$_2$O$_2$ or addition of 150 µM exogenous H$_2$O$_2$ to ECaNEp cells did not lead to detectable CM-H$_2$DCFDA oxidation in the cytosol, nor did it lead to cell death within 1 hour. This indicates that close contact between mycoplasmas and host cells is necessary to successfully target the toxic compounds to the host cells. In this context, it is worth noting that *M. mycoides* subsp. *mycoides* SC—and most other pathogenic mycoplasmas for that matter—tightly attach to their host cells, but do not penetrate. Moreover, active uptake of glycerol is necessary to obtain the glycerol-induced cytotoxic effect on ECaNEp cells. The European strain L2 of *M. mycoides* subsp. *mycoides* SC, which is devoid of the GtsABC transporter required for active uptake of glycerol and which produces 10 times less H$_2$O$_2$ at a significant lower rate, has only a weak cytotoxic effect on ECaNEp cells under identical experimental conditions. The residual uptake of glycerol by strain L2 is thought to occur by means of a less efficient transport pathway mediated by the putative glycerol facilitator factor GlpF.

Based on our results, we propose the following model for triggering cellular damage to eukaryotic cells by *M. mycoides* subsp. *mycoides* SC (FIG. 4): glycerol present in the interstitial fluid is incorporated actively via the highly active ABC glycerol transporter (GtsA, GtsB and GtsC) and is subsequently phosphorylated into glycerol-3-phosphate. This, in turn, is oxidized in the presence of O$_2$ by GlpO into DHAP, which enters in the glycolytic pathway, and produces one molecule of H$_2$O$_2$. Facilitated by the intimate contact of the mycoplasma with the host cell membrane, H$_2$O$_2$ and accompanying ROS enter the host cell. Inside the host cells, H$_2$O$_2$ and ROS act as powerful mediators of cell injury and inducers of inflammatory processes. They are expected to damage the host either by directly impairing tissue cells or inducing host gene expression, e.g., pro-inflammatory genes via activation of NF-κB, or via the Fenton reaction (Crichton, R. R. et al. 2002, J. Inorg. Biochem. 91: 9-18). Interestingly, mycoplasmas have previously been shown to induce a respiratory burst in phagocyte cells suggesting that host-generated ROS might further contribute to tissue damage.

H$_2$O$_2$ and ROS can also activate NF-κB and, by doing so, induce the expression of a range of immune and pro-inflammatory genes in the eukaryotic host, a mechanism that might be of particular importance in respiratory tract infections caused by mycoplasmas.

Vaccines based upon mycoplasmal L-α-glycerophosphate oxidase or antibodies against mycoplasmal L-α-glycerophosphate oxidase successfully suppress the production of H$_2$O$_2$ and ROS, and by doing so, they prevent host cell damage, inflammation and disease.

Legend to the Figure.

FIG. 1. Location and activity of mycoplasmal L-α-glycerophosphate oxidase., Scanning electron microscopy photographs showing *M. mycoides* subsp. *mycoides* SC strain Afadé labelled with a 15 nm colloidal gold-conjugated secondary antibody (a) on the cell surface when incubated with IgG from anti-GlpO; (b) back scattered when incubated with IgG from anti-GlpO; (c) on the cell surface when incubated with pre-immune serum; and (d) back scattered when incubated with pre-immune serum Scale bar, 500 nm. (e), Immunoblot analysis of electron Triton X-114-fractionated total antigens of *M. mycoides* subsp. *mycoides* SC strain Afadé with GlpO antiserum. Lane 1, detergent phase, 20 µg of proteins; lane 2, aqueous phase, 20 µg of proteins; Std, molecular mass standard. (f), Hydrogen peroxide production of *M. mycoides* subsp. *mycoides* SC strain Afadé after addition of 100 µM glycerol. The data shown are the mean values of five independent measurements. Standard deviations of the individual measurements were below 5% of the mean values. Triangles and solid line, untreated *M. mycoides* subsp. *mycoides* SC; crosses and dashed line, *M. mycoides* subsp. *mycoides* SC pre-treated with Fab fragments from anti-GlpO IgG; squares and dotted line, *M mycoides* subsp. *mycoides* SC pre-treated with Fab fragments from anti-LppC.

FIG. 2. Cytotoxicity of *M. mycoides* subsp. *mycoides* SC to ECaNEp cells (a-f) and cell viability assay (g). a, ECaNEp cells (control); b, ECaNEp 1 h after infection with *M. mycoides* subsp. *mycoides* SC strain Afadé; c, ECaNEp 1 h after infection with strain Afadé in the presence of glycerol (100 µM); d, ECaNEp 1 h after infection in the presence of glycerol (100 µM) with strain Afadé pre-treated with Fab fragments from anti-GlpO IgG; e, ECaNEp 1 h after infection in the presence of glycerol (100 µM) with strain Afadé pre-treated with Fab fragments from anti-LppC IgG; f, ECaNEp cells infected with *M. mycoides* subsp. *mycoides* SC strain L2 (which lacks an active glycerol uptake system) in the presence of glycerol (100 µM). The MOI in all experiments was of 50 mycoplasmas per cell. g, Viable ECaNEp cells at different times following infection with *M. mycoides* subsp. *mycoides* SC strain Afadé at a MOI of 50 mycoplasmas per cell. Triangles and thick solid line, infection with strain Afadé in presence of 100 µM glycerol; crosses and dotted line, infection in presence of 100 µM glycerol with strain Afadé SC pre-treated with anti-GlpO Fab fragments (0.26 μg/ml); squares and dashed line, strain Afadé infection without glycerol; diamonds and thin solid line, ECaNEP cells alone (control).

FIG. 3. Detection of intracellular $H_2O_2$ and ROS in ECaNEp cells infected with *M mycoides* subsp. *mycoides* SC strain Afadé at a MOI of 500 mycoplasmas per cell or treated with $H_2O_2$. Phase contrast micrographs and fluorescence micrographs of ECaNEp cells: 20 min after infection with *M mycoides* subsp. *mycoides* SC strain Afadé in the absence of glycerol [(a) phase contrast micrograph, and (b) fluorescence micrograph]; infected with strain Afadé in medium supplemented with glycerol [(c) phase contrast micrograph, and (d) fluorescence micrograph]; infected in medium supplemented with glycerol with strain Afadé pre-treated with Fab fragments from anti-GlpO IgG [(e) phase contrast micrograph, and (f) fluorescence micrograph]; pre-treated with N-acetyl-L-cysteine and then infected with strain Afadé in medium with glycerol [(g) phase contrast micrograph, and (h) fluorescence micrograph]; incubated for 20 min in medium supplemented with 4.4 mM $H_2O_2$ [(i) phase contrast micrograph, and (j) fluorescence micrograph].

Figure 4:
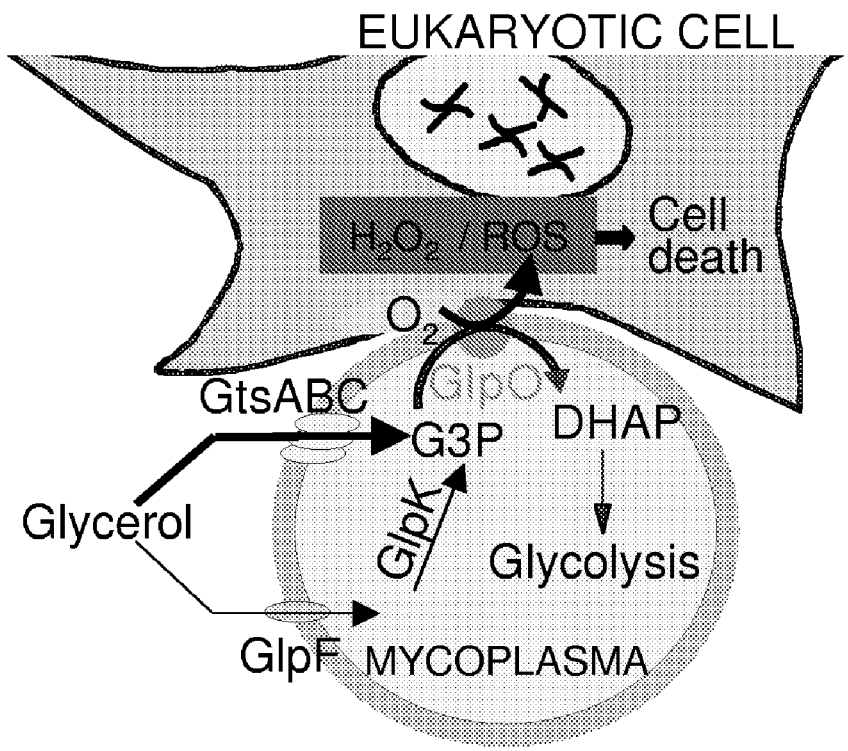

FIG. 4. Model for triggering host cell inflammation by *M. mycoides* subsp. *mycoides* SC. GtsABC: active glycerol transport and phosphorylation system; GlpF: glycerol facilitator factor; GlpK: glycerol kinase; G3P: glycerol-3-phosphate; DHAP: dihydroxyacetone phosphate; GlpO: mycoplasmal L-α-glycerophosphate oxidase. Thick arrows indicate the main virulence pathway of *M. mycoides* subsp. *mycoides* SC.

TABLE 1

Comparison of the protein sequences of GlpO and GtsABC from *M. mycoides* subsp. *mycoides* SC strain Afade with sequences of the homologues from other mycoplasmas.
GlpO (CAE46342)

| Mycoplasma | Protein name[1] | EMBL/ GenBank accession number | Identity (%) | Similarity (%) |
|---|---|---|---|---|
| *M.* sp.bovine group 7 | GlpO | CAE46341 | 99 | 99 |
| *M. mycoides* subsp. *capri* | GlpO | CAE46343 | 97 | 99 |
| *M. penetrans* | GlpA | BAC44427 | 58 | 75 |
| *M. gallisepticum* | MGA_0646 | AAP56366 | 52 | 73 |
| *M. mobile* | GlpO | AAT27781 | 52 | 71 |
| *M. pulmonis* | GlpD | CAC13437 | 46 | 70 |
| *M. hyopneumoniae* | GlpD | AAV27992 | 44 | 64 |
| *M. pneumoniae* | GlpD | AAB95751 | 44 | 64 |
| *M. genitalium* | MG039 | AAC71255 | 40 | 62 |

The invention claimed is:

1. A method for inducing the production of antibodies against mycoplasmal L-α-glycerophosphate oxidase in an animal, comprising administering to the animal an immunogenically effective amount of isolated and purified mycoplasmal L-α-glycerophosphate oxidase and a pharmaceutically acceptable carrier.

2. The method according to claim 1, comprising additionally administering at least one antigen from another microorganism or virus that is pathogenic to the same animal.

3. The method according to claim 2, wherein said virus or micro-organism is selected from the group consisting of Pseudorabies virus, Porcine influenza virus, Porcine parvo virus, Transmissible gastro-enteritis virus, Rotavirus, *Mycoplasma hyopneumoniae, Brachyspira hyodysenteriae, Escherichia coli, Leptospira* spp, *Erysipelothrix rhusiopathiae, Bordetella bronchiseptica, Brachyspira hyodysenteriae, Shigella* sp., *Salmonella choleraesuis, Salmonella typhimurium, Salmonella enteritidis, Haemophilus parasuis, Lawsonia, Pasteurella multocida, Streptococcus suis, Actinobacillus pleuropneumoniae, Staphylococcus hyicus* and *Clostridium perfringens*.

4. The method according to claim 2, wherein said virus or micro-organism is selected from the group consisting of Bovine Herpesvirus, bovine Viral Diarrhoea virus, Parainfluenza type 3 virus, Bovine Paramyxovirus, Foot and Mouth Disease virus, Bovine Respiratory Syncytial Virus, porcine circo virus, porcine respiratory reproductive syndrome virus, *Mycoplasma* spp., *Pasteurella haemolytica, Staphylococcus aureus, Escherichia coli, Leptospira* spp., *Staphylococcus uberis, Theileria parva, Theileria annulata, Babesia bovis, Babesia bigemina, Babesia major, Trypanosoma* species, *Anaplasma marginale, Anaplasma centrale* and *Neospora caninum*.

5. The method according to claim 2, wherein said virus or micro-organism is selected from the group consisting of Fowlpox virus, Infectious Bronchitis virus, Infectious Bursal Disease Virus, Marek's Disease Virus, Chicken Anaemia agent, Avian Reovirus, Turkey Rhinotracheitis virus, Chicken Poxvirus, Avian Encephalomyelitisvirus, Duck Plague virus, Newcastle Disease virus, Egg prop syndrome virus, Infectious Laryngotracheitis virus, Herpes Virus of Turkeys, *Haemophilus paragallinarum, Ornithobacterium rhinotracheale, Salmonella* species, *Campylobacter* species and *Eimeria* species.

6. The method according to claim 2, wherein said virus or micro-organism is selected from the group consisting of influenza virus, measles virus, mumps paramyxovirus, *Clostridium diphteriae, Clostridium tetani, Bordetella pertussis*, and pox virus.

7. The method according to claim 1, wherein an adjuvant is also administered.

8. The method according to claim 1, wherein said mycoplasmal L-α-glycerophosphate oxidase is encoded by the GlpO gene of the *Mycoplasma* species selected from the group consisting of *M. bovis, M.* sp.bovine group 7, *M. mycoides* subsp. *Capri, M. penetrans, M. gallisepticum, M. synoviae, M. mobile, M. pulmonis, M. hyopneumoniae, M. pneumoniae, M. genitalium, M. mycoides* S(mall) C(olony) strain Afadé and *M. mycoides* S(mall) C(olony) strain L2.

9. The method of claim 1, comprising administering in addition a whole cell *Mycoplasma* preparation.

10. The method of claim 1, comprising administering in addition a whole cell *Mycoplasma* preparation.

11. The method of claim 1, wherein said mycoplasmal L-α-glycerophosphate oxidase is encoded by the GlpO gene of the *Mycoplasma* species selected from the group consisting of *M.* sp.bovine group 7, *M. mycoides* subsp. *Capri, M. penetrans, M. gallisepticum, M. mobile, M. pulmonis, M. hyopneumoniae, M. pneumoniae*, and *M. genitalium*.

* * * * *

```
                        SEQUENCE LISTING

<160> NUMBER OF SEQ ID NOS: 6

<210> SEQ ID NO 1
<211> LENGTH: 35
<212> TYPE: DNA
<213> ORGANISM: Mycoplasma sp.

<400> SEQUENCE: 1
ttgcggccgc atttccatgg aagaatagct tcttc                                 35

<210> SEQ ID NO 2
<211> LENGTH: 35
<212> TYPE: DNA
<213> ORGANISM: Mycoplasma sp.

<400> SEQUENCE: 2
tcgaattcaa tgaagcaaac aaaagttgat atttg                                 35

<210> SEQ ID NO 3
<211> LENGTH: 24
<212> TYPE: DNA
<213> ORGANISM: Mycoplasma sp.

<400> SEQUENCE: 3
tggttgccaa ttagccttttt tatc                                            24

<210> SEQ ID NO 4
<211> LENGTH: 23
<212> TYPE: DNA
<213> ORGANISM: Mycoplasma sp.

<400> SEQUENCE: 4
gctaattggc aaccaaaaga aga                                              23
```

```
<210> SEQ ID NO 5
<211> LENGTH: 24
<212> TYPE: DNA
<213> ORGANISM: Mycoplasma sp.

<400> SEQUENCE: 5
tttgatccag tcttcataac gttt                                          24

<210> SEQ ID NO 6
<211> LENGTH: 23
<212> TYPE: DNA
<213> ORGANISM: Mycoplasma sp.

<400> SEQUENCE: 6
gaagactgga tcaaagaaat gga                                           23
```